United States Patent [19]
Allemand et al.

[11] Patent Number: 4,772,126
[45] Date of Patent: Sep. 20, 1988

[54] PARTICLE DETECTION METHOD AND APPARATUS

[75] Inventors: Charly D. Allemand, Newton, Mass.; Hitoshi Iida, Gillette, N.J.; Mario A. Maldari, Stow, Mass.

[73] Assignee: Inspex Incorporated, Waltham, Mass.

[21] Appl. No.: 922,478

[22] Filed: Oct. 23, 1986

[51] Int. Cl.⁴ ............................................. G01N 15/02
[52] U.S. Cl. ...................................... 356/336; 356/337
[58] Field of Search ............... 356/335, 336, 337, 237; 250/562, 572; 358/107

[56] References Cited
U.S. PATENT DOCUMENTS
4,377,340 3/1983 Green et al. .................... 356/237

*Primary Examiner*—Gene Wan
*Attorney, Agent, or Firm*—Irving M. Kriegsman

[57] ABSTRACT

An apparatus and method are disclosed for detecting the presence of particles on the surface of an object such as the front side of a patterned semiconductor wafer. A vertically expanded, horizontally scanning, beam of light is directed onto an area on the surface of the object at a grazing angle of incidence. A video camera positioned above the surface detects light scattered from any particles which may be present on the surface, but not specularly reflected light. The surface is angularly prepositioned (rotated) relative to the incident light beam so that the diffracted light from the surface and the pattern of lines on the surface is at a minimum. The object is then moved translationally to expose another area to the incident light beam so that the entire surface of the object or selected portions thereof can be examined, an area at a time.

26 Claims, 3 Drawing Sheets

PARTICLE DETECTION METHOD AND APPARATUS

BACKGROUND OF THE INVENTION

The present invention relates generally to a method and apparatus for detecting the presence of particles on the surface of an object and more particularly to a method and apparatus for detecting and measuring the number and sizes of contaminant particles on the surface of an object such as a patterned semiconductor wafer using the principle of scattered light.

Although the invention will hereinafter be described specifically in connection with detecting particles on the surface of a patterned semiconductor wafer, it is to be understood that the invention is not limited to a surface on that particular type of object but rather is useful in detecting the presence of particles on the surface of other objects such as virgin semiconductor wafers, filmed semiconductor wafers and coated or uncoated aluminum memory discs.

In the prior art there are a variety of ways of detecting and measuring the number and sizes of particles on the surface of a semiconductor wafer for the purpose of rejecting those wafers which have on their surface one or more particles above certain sizes or for those having on their surface an excessive number of particles.

One of the most prevalent methods employs the human operator using a light field/dark field microscope. Using the eye, the operator actually counts the number of particles and also identifies the size of the particles, such as those between 1 to 20 microns, and then rejects those wafers which have an excessive number of particles or those having particles of or above a certain size. This method is without doubt highly inaccurate and very expensive both in terms of wages for the human operator and in terms of the number of rejects both after the inspection and after production of the chips (when an erroneously passed wafer is found to have an electrical defect, e.g. short circuits, because of the presence of contaminant particles).

In U.S. Pat. No. 4,377,340 to G. P. Green etc., there is disclosed a method and apparatus for detecting and measuring the number and sizes of impurities on the surface of a material, such as a semiconductor wafer, wherein a beam of high intensity collimated light from a xenon arc lamp is directed onto the surface at normal incidence in the absence of any extraneous light, through a collimating mirror and a pin hole device and whereat the particles will scatter the light, and wherein the surface is viewed by a high light sensitive TV camera which is positioned off-axis to pick up scattered light but not specularly reflected light for display on a viewing screen.

In IBM Technical Disclosure Bulletin Volume 2, No. 10, pages 1672–1673, dated March, 1970, there is disclosed a system for detecting repeated geometric defects on a reflecting surface in which a collimated light beam strikes the surface being examined at a infinite angle of incidence is directed through a telescope to a photomultiplier tube.

In IBM Technical Disclosure Bulletin Volume 21, No. 6, pages 2336–2337 dated November, 1978, there is disclosed a system for detecting defects on wafers wherein light from a plurality of ring light sources impinges on the wafer at an oblique angle to the wafer surface and wherein light scattered upward from the surface at right angles thereto is fed by a lens system into a broad band array detector.

In U.S. Pat. No. 2,947,212 to R. C. Woods there is disclosed a method of detecting surface conditions on a strip of sheet metal having line markings in which light from a light source is directed toward the surface of the sheet metal in a direction generally perpendicular to the line markings. Non-specular reflection in a selected direction which is perpendicular to the lines, and which is preferably between the angle of incidence and the angle of specular reflection, is monitored by a photoelectric cell which is able to detect a surface flaw by variation in the intensity of the reflected light. The light in the incident beam may be polarized and the light in the selected non-specular reflected beam filtered to pass only such polarized light.

In U.S. Pat. No. 4,342,515 to Akiba et al there is disclosed an inspection apparatus for detecting unfavorable foreign matters existent on the surface of an object such as a semiconductor wafer. The apparatus includes a collimated beam generator portion which projects a collimated beam toward the object to-be-inspected from a side thereof and a mechanism which senses light reflected from the surface of the object, through a polarizer plate. In accordance with the disclosed technique for using the apparatus, the signal-to-noise ratio between a detection signal generated by a pattern of the foreign matter to-be-detected and a signal generated by a normal pattern of the object surface and sensed as a noise component can be enhanced.

In U.S. Pat. No. 3,782,836 to Fey et al there is disclosed a surface irregularity analyzing system which includes structure for directing light toward a surface in a direction having a certain angular relationship to the surface. If the light stikes irregularities in the surface it is reflected in a direction having an angular relationship to the surface other than equal and opposite the incident direction. The amount of light reflected from irregularities in the surface is determined, either photographically or photoelectrically, to provide an analysis or irregularities in the surface.

It is an object of this invention to provide a new and improved method and apparatus in detecting the presence of contaminant particles on a surface using the principle of scattered light.

It is another object of this invention to provide a method and apparatus as described above in which the surface being examined is the surface of a semiconductor wafer having a printed circuit pattern formed on it.

It is still another object of this invention to provide a novel optical arrangement for illuminating a surface for the purpose of detecting light scattered by unwanted particles which may be present on the surface.

It is yet still another object of this invention to provide a method and apparatus for detecting particles on a surface which involves illuminating the surface at a grazing angle of incidence with a vertically expanded and horizontally scanning beam of laser light.

It is a further object of this invention to provide a method and apparatus as described above in which the scattered light is detected by a video camera.

It is another object of this invention to provide a method and apparatus as described above wherein unwanted reflected light from the surface and/or from a printed circuit pattern of lines which may be present on the surface is reduced to a minimum.

It is still another object of this invention to provide a method and apparatus as described above in which the surface being examined is illuminated, an area at a time.

It is yet still another object of this invention to provide method and apparatus as described above in which the signal to noise ratio between scattered light from particles and diffracted light from the surface itself is maximized.

It is a further object of this invention to provide a system designed especially for use in dark field illumination applications.

The foregoing and other objects as well as many advantages of the invention will appear from the description to follow. In the description, reference is made to the accompanying drawing which forms a part thereof, and in which is shown by way of illustration, a specific embodiment for practicing the invention. This embodiment will be described in sufficient detail to enable those skilled in the art to practice the invention, and it is to be understood that other embodiments may be utilized and that structural changes may be made without departing from the scope of the invention. The following detailed description is, therefore, not to taken in a limiting sense, and the scope of the present invention is best defined by the appended claims.

SUMMARY OF THE INVENTION

Apparatus for use in detecting particles on the surface of an object constructed according to the teachings of the present invention comprises a holder for holding the object to be examined, means for moving the holder translationally about two mutually perpendicular axes so that different areas on the surface can be examined, means for rotating the holder about an axis perpendicular to the plane defined by the two mutually perpendicular axes so that the surface can be oriented relative to an incident beam to where the diffracted light from the surface is at a minimum, means for illuminating an area on the surface of the object at grazing angle of incidence with a beam of laser light that is expanded in one direction and scanning in another direction, perpendicular to the direction in which it is expanded and camera means disposed above the object for detecting light scattered from any particles which may be present on the surface.

A method for detecting particles on the surface of an object according to this invention comprises directing a beam of laser. light expanded in one direction and scanning in another direction, perpendicular to the direction in which it is expanded onto an area on the surface of the object at a grazing angle of incidence, positioning a video camera above the object orienting the surface of the object relative to the incident light beam so that the diffracted light from the surface and/or a pattern that may be formed on the surface is at a minimum and then detecting light scattered from the surface with the video camera.

BRIEF DESCRIPTION OF THE DRAWINGS

In the drawings wherein like reference numerals represent like parts.

DETAILED DESCRIPTION OF PREFERRED EMBODIMENTS

The present invention is directed to a method and apparatus for detecting the presence of particles on the surface of an object using the principle of scattered light.

In accordance with the invention an area on the surface to be examined is illuminated with a beam of laser light at grazing angle of incidence. The beam of laser light is expanded vertically and scanning horizontally so that the area on the surface that is illuminated is generally rectangularly shaped. A video camera is positioned above the surface of the object. Light scattered by any particles which may be present on the area that is illuminated is detected by the video camera over a field of view defined by the objective lens inside the camera. Because of the angle at which the incident light beam strikes the surface and the positioning of the camera, specularly reflected light from the surface is not picked up by the camera. The surface is oriented relative to the incident light beam to a position where the diffracted light from the area illuminated is at a minimum. The output of the video camera is processed in a computer and then displayed on a monitor. The object is then moved translationally relative to the incident light beam so that another area can be examined and so forth. Using the invention, particles on the order of 1 micron and less can be repeatedly detected.

Figure 1:
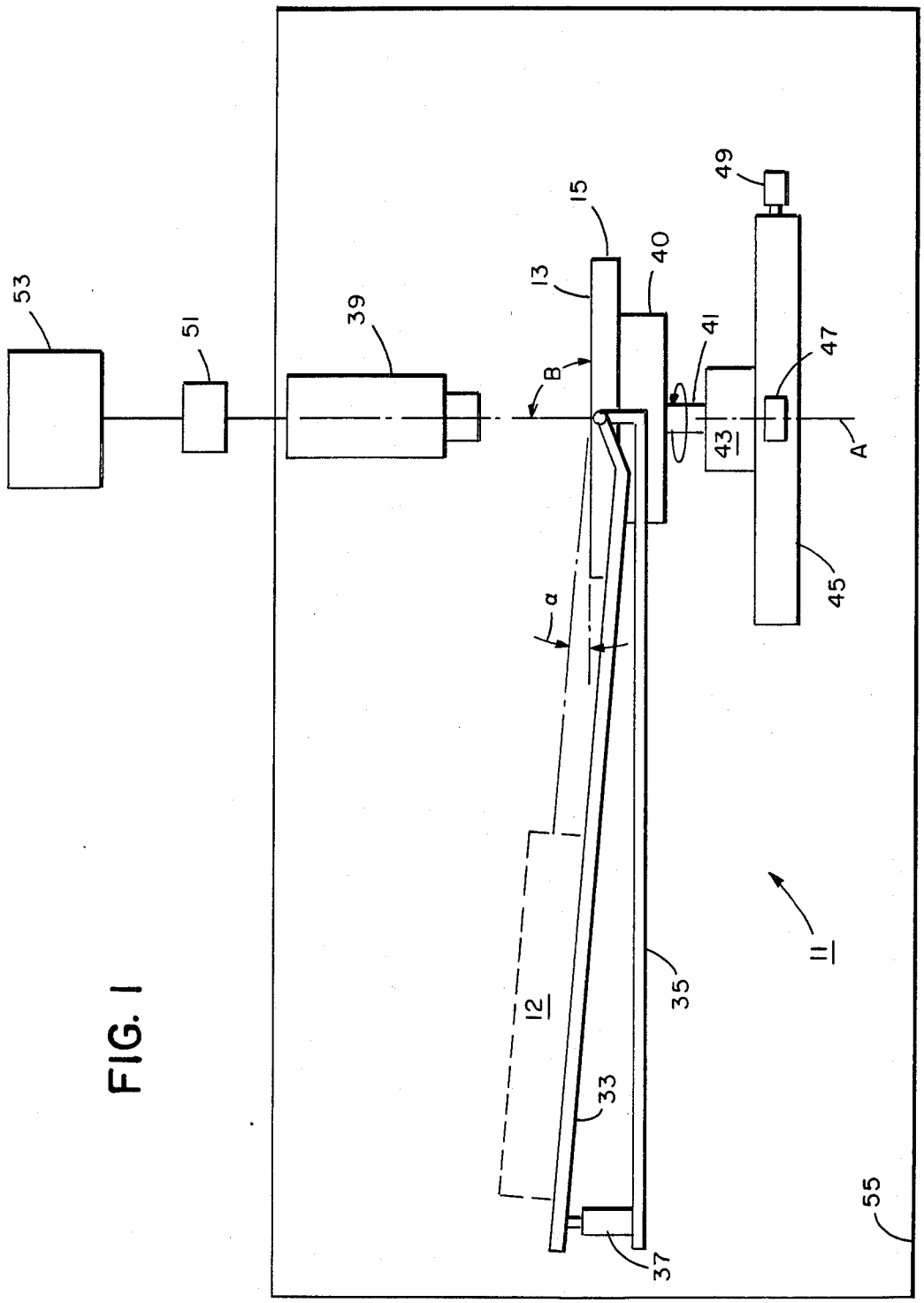
FIG. 1 is a schematic representation of an embodiment of an apparatus constructed according to the teaching of the present invention for detecting the presence of particles on the surface of a patterned semiconductor wafer.

Referring now to the drawings there is illustrated in FIG. 1 an apparatus 11 constructed according to the present invention for use in detecting the presence of particles on the surface of an object. For illustrative purposes, the surface examined is shown as being the top surface 13 of a patterned semiconductor wafer 15.

As is known, a patterned semiconductor is a wafer in which a printed circuit has been formed on its top surface. Generally speaking, in most all patterned semiconductor wafers the pattern of lines which make up the actual printed circuit extend mainly in two mutually perpendicular directions.

Apparatus 11 includes a light beam gathering section which is shown in FIG. 1 symbollically as a dotted line rectangle numbered 12. Light beam generating section 12, which is also shown in detail in FIG. 2, includes a laser light source 17, such as a helium-neon laser, for generating a high intensity collimated beam of light. The beam of light produced by light source 17 which is polarized, is circular in cross-section and has a diameter of about 0.8 mm. is caused to diverge in the vertical direction and remain collimated in the horizontal direction by means of a first cylindrical lens 19. A spherical lens 21 collimates the beam of light passed by first cylindrical lens 19 in the vertical direction so that it has a height of about 2 mm. and causes the beam to converge in the horizontal direction where it is brought to focus on the mirror 23 of a scanning galvanometer 25. The light beam deflected by the scanning galvanometer 25, which is diverging in the horizontal direction, collimated in the vertical direction and scanning horizontally is passed through a second cylindrical lens 29 which is at a distance from scanning galvanometer 25 equal to its focal length. Second cylindrical lens 29 collimates the light beam in the horizontal direction so that it has a width of about 0.8 mm. while leaving the beam collimated in the vertical direction. Galvanometer scanner 25 includes an adjusting knob 31 which enables the amplitude and hence the distance of the sweep to be varied.

The light beam passed by the second cylindrial lens 29 which is expanded vertically and scanning horizontally is directed onto the top surface 13 of semiconductor wafer 15 at a grazing angle of incidence (i.e. an angle of between around 85 and 90 degrees from the normal), the polarization of the light beam being perpendicular to the plane of incidence and the area on the surface 13 being illuminated by the light beam defined by a rectangle labelled A-B-C-D. As can be appreciated, the intensity of the light striking surface 13 will not be uniform over the entire area A-B-C-D but rather will decrease towards edge CD. Over area E-F-G-H, however, the intensity is relatively uniform.

Figure 2:
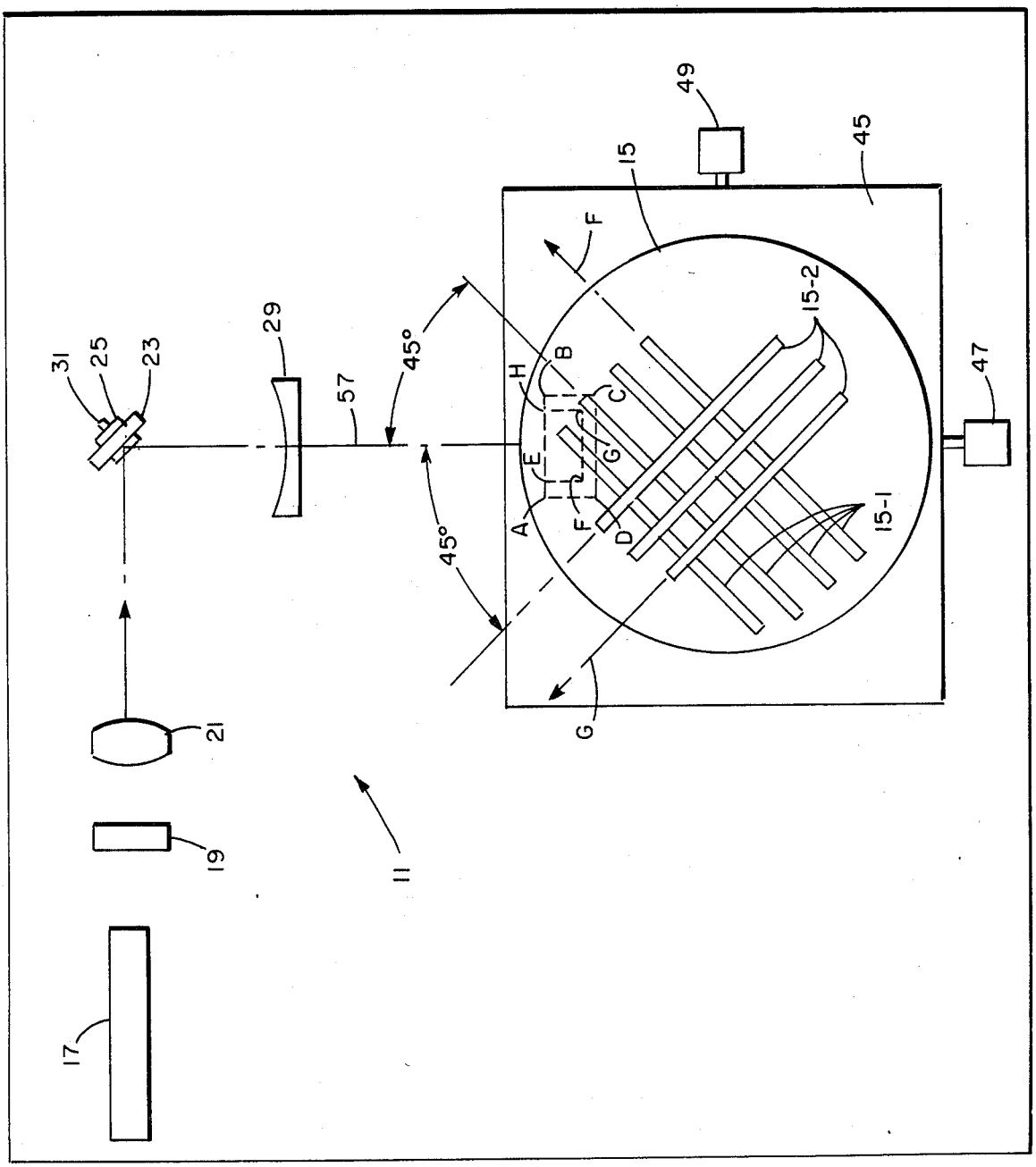
FIG. 2 is a plan view of a portion of the apparatus and wafer shown in FIG. 1, illustrating how the wafer is angularly oriented relative to the incident light beam.

As can be seen in FIG. 2, semiconductor wafer 15 has a pattern of lines making up the printed circuit formed on it, the pattern of lines comprising a first plurality of parallel lines 15-1 disposed in a first direction F and a second plurality of parallel lines 15-2 disposed in a second direction G which is perpendicular to the first direction. For simplicity, the pattern of lines is not shown in FIG. 1. In accordance with the invention, semiconductor wafer 15 is postioned so that the incident light beam strikes the surface at an angle of 45 degrees to each set of parallel lines, this angular position being where diffracted light from the patterned surface is at a minimum.

The components making up light beam generating section 12 are mounted on a bifurcated plate 33 which is hinged at one end to a base 35. A drive mechanism 37 connected between plate 33 and base 35 enables the angle between plate 33 and base 35 and hence the angle of incidence of the light beam to be selectively varied.

A high sensitivity video camera 39, such as model C1000-12 manufactured by Hamamatsu TV Co. Ltd of Japan, is positioned above wafer 15 at an angle in the vicinity of 90 degrees for detecting light scattered from any particles present on the surface 13, the exact angle being where the diffracted light received by camera 39 is at a minimum.

Wafer 15 is seated on a holder 40 which is in the form of a vacuum chuck. Holder 40 is mounted on a vertical shaft 41 which is rotable about its longitudinal axis A by means of a motor 43 so that wafer 15 can be rotated relative to the incident light beam to the angular position noted above where the diffracted light is at a minimum. Motor 43 is mounted on a platform 45 which is movable translationally in two mutually perpendicular directions by two stepping drive motors 47 and 49 so that the entire surface of wafer 15 can be illuminated, an area at a time, by the impinging beam of light.

Camera 39 is connected to a computer 51 which is coupled to a monitor or display 53. The entire apparatus 11 except for the computer and display is enclosed within a light tight housing 55.

Apparatus 11 is used in the following manner. A Wafer 15 to be examined is placed on holder 40. With wafer 15 stationary, an area on surface 13 defined by rectangle A-B-C-D is illuminated with the horizontally scanning, vertically expanded beam of light from optics 12. Camera 39 is then brought to focus over the part E-F-G-H of area A-B-C-D where the intensity of the incident light is uniform. Wafer 15 is then rotated about an axis perpendicular to the plane of the wafer (by rotating holder 40 about axis A), observing the diffracted or background light picked up by camera 39 as wafer 15 turns, so as to obtain the desired angular position relative to the incident light beam 57 where the diffracted light from the wafer surface itself and the pattern of lines on the wafer 15 is at a mimimum. For a patterned semiconductor wafer such as wafer 15 having two sets of mutually perpendicular pattern lines, the angle is 45 degrees to the two sets of pattern lines, as shown. Also, plate 33 is angularly adjusted to the exact grazing angle where the diffracted light received by camera 39 is at a minimum and camera 39 tilted to the angle B where the diffracted light is at a minimum. With wafer 15 at the optimum angular position as shown in FIG. 2 and stationary, the light scattered is detected by camera 39, processed in computer 51 and displayed on display 53. Wafer 15 is then moved translationally, by moving platform 45, so that other areas on surface 13 may be examined, an area at a time, as desired.

Figure 3:
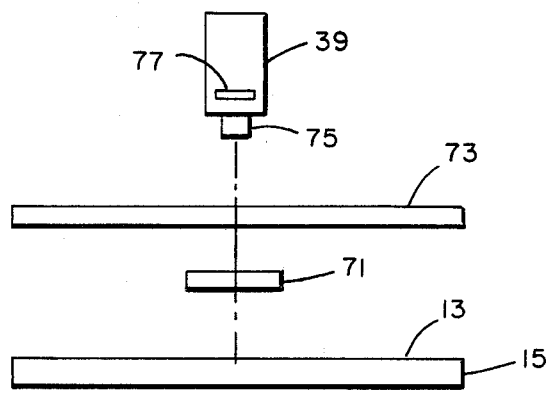
FIG. 3 shows a modification of a portion of the apparatus shown in FIG. 2.

In FIG. 3 there is shown a modification of the readout portion of the appartus in which the diffracted light from surface 13 and the pattern of lines on surface 13 is further minimized. A lens 71 disposed above surface 13 forms a Fourier transform of surface 13 on a mask 73. Mask 73 contains a pattern corresponding to the Fourier transform of the patterned surface. Thus, all of the light from surface 13 but not light scattered from any particles on the surface will be masked off. Lens 75 of camera 39 images surface 13 on the target 77 of camera 39.

Figure 4:
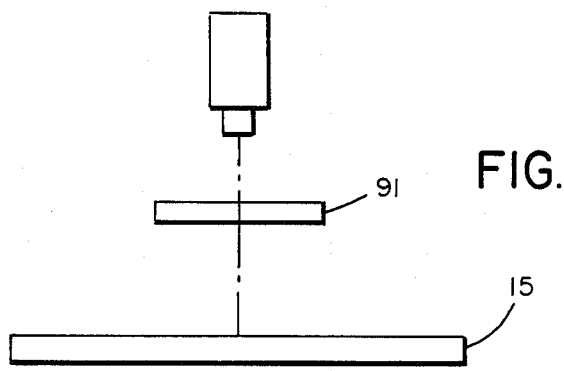
FIG. 4 shows still another modification of a portion of the apparatus shown in FIG. 2.

In still another modification of the invention, which is shown in FIG. 4, the signal-to-noise ratio between scattered light and background light is further improved by positioning a polarizer 91, which is cross-polarized realtive to the polarization of the incident light beam, in front of camera 39.

Figure 5:
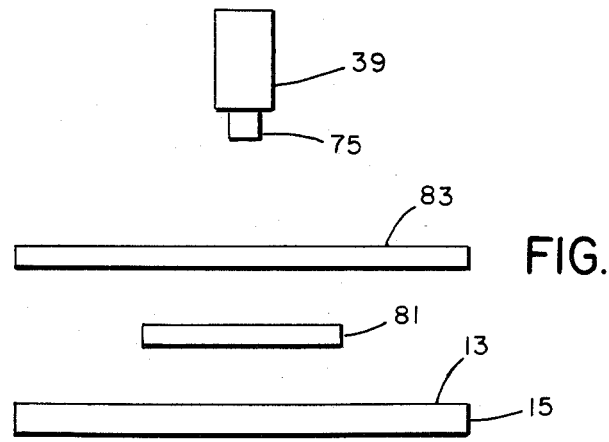
FIG. 5 shows a further modification of a portion of the apparatus shown in FIG. 2.

In a further modification shown in FIG. 5 a lens 81 forms an image of surface 13 on mask 83. Mask 83 contains a pattern corresponding to all predetermined unwanted light. Objective lens 75 of camera 39 is brought to focus on mask 81 over an area of interest.

The embodiments of the present invention are intended to be merely exemplary and those skilled in the art shall be able to make numerous variations and modifications to it without departing from the spirit of the present invention. For example, instead of being expanded vertically and scanning horizontally, the impinging light beam could be expanded horizontally and made scanning vertically. All such variations and modifications are intended to be within the scope of the present invention as defined in the appended claims.

What is claimed is:

1. Apparatus for use in detecting particles on a surface of an object comprising:
  a. a holder for holding said object,
  b. means for illuminating an area on the surface with a collimated beam of light at grazing angle of incidence, and
  c. camera means for detecting light scattered from said area on the surface by any particles present on the surface at that area, the intensity of the scattered light being proportional to the size of the particles.

2. The apparatus of claim 1 and wherein the collimated beam of light is a beam of light from a laser that has been made scanning in one direction so as to increase the size of the area illuminated by the light beam.

3. The apparatus of claim 2 and wherein the holder is mounted for rotational movement about an axis.

4. The apparatus of claim 3 and wherein the beam of light is expanded in a direction perpendicular to the direction in which it is made scanning so as to further increase the size of the area illuminated by the beam of light.

5. The apparatus of claim 4 and wherein the camera means comprises a camera which is disposed above the surface at an angle with said surface in the vicinity of ninety degrees.

6. The apparatus of claim 5 and wherein the camera is a video camera.

7. The apparatus of claim 6 and wherein the illuminating means comprises a laser for producing a collimated beam of light, a first cylindrical lens for causing the collimated beam of light from the laser to diverge in a first direction and remain collimated in a second direction, a spherical lens for causing the beam of light from the first cylindrical lens to be collimated in the first direction and converge in the second direction, a scanner for causing the beam of light from the spherical lens to scan and to diverge in the first direction and be collimated in the second direction and a second cylindrical lens for collimating the scanning beam of light from the scanner in the first direction and leaving the beam collimated in the second direction.

8. The apparatus of claim 7 and further including a computer coupled to the camera for storing and/or processing information from the camera and a display coupled to the computer for displaying the stored and/or processed information.

9. The apparatus of claim 7 and further including a mask positioned between the surface and the camera, said mask having a pattern corresponding to the Fourier transform of the surface in the absence of particles, and a lens disposed between the surface and the mask for forming a Fourier transform of the surface of the mask.

10. The apparatus of claim 7 and wherein the light beam from the laser is polarized and the apparatus further includes a polarizer between the surface and the video camera, the polarizer being cross-polarized relative to the polarization of the light beam from the laser.

11. The apparatus of claim 7 and further including a mask having a pattern of all unwanted light disposed between the surface and the video camera and a lens for imaging the surface of the mask.

12. The apparatus of claim 7 and wherein the laser is a helium-neon laser and the scanner is a scanning galvanometer.

13. The apparatus of claim 7 and wherein the holder is mounted for translational movement about two mutually perpendicular axes which define a plane perpendicular to the axis of rotation so that the impinging light beam can be moved from one area to another on the surface.

14. The apparatus of claim 7 and further including a base and a plate hingedly mounted on the base and wherein the illuminating means is mounted on the plate.

15. A method of detecting particles on an area of a surface of an object comprising:
a. directing a collimated beam of light onto said area of the surface of the object at grazing angle of incidence, whereby said particles will scatter light with intensities proportional to the sizes of said particles,
b. orienting said surface relative to the incident light beam so that diffracted light from said surface itself and any pattern which may be on the surface is reduced to a minimum, and
c. detecting light scattered from particles which might be present on the area of the surface.

16. The method of claim 4 and wherein detecting the light scattered comprises focussing a video camera on at least a portion of the area illuminated by said beam of light.

17. The method of claim 5 and wherein orienting the surface comprises rotating the object about an axis perpendicular to the plane of the surface.

18. The method of claim 15 and wherein the light beam is scanning.

19. The method of claim 18 and further including adjusting the angular position of the camera so that diffracted light received by the camera is reduced.

20. Apparatus for detecting particles on an area of a surface of a semiconductor wafer having a printed circuit pattern thereon comprising:
a. holder for holding said semiconductor wafer,
b. means for illuminating said area on said surface at grazing angle of incidence with a beam of light from a laser that has been expanded in one direction and made scanning in another direction, perpendicular to the direction in which it is expanded.
c. means for rotating the holder about an axis normal to the surface so that light diffracted from the surface and the pattern thereon can be reduced to a minimum, and
d. a video camera disposed above said surface at an angle in the vicinity of ninety degrees to detect light scattered from the area on the surface by any particles thereon and not specularly reflected light.

21. The apparatus of claim 20 and wherein the illuminating means comprise a laser for producing a collimated beam of light, a first cylindrical lens for causing the collimated beam of light from the laser to diverge in a first direction and remain collimated in a second direction, a spherical lens for causing the beam of light from the first cylindrical lens to be collimated in the first direction and converge in the second direction, a scanner for causing the beam of light from the sperical lens to scan and to diverge in the first direction and be collimated in the second direction and a second cylindrical lens for collimating the scanning beam of light from the scanner in the first direction and leaving the beam collimated in the second direction.

22. A method of detecting particles on a surface of a semiconductor wafer having a printed circuit pattern thereon comprising:
a. directing a collimated beam of light from a laser that has been expanded in one direction and made scanning in another direction perpendicular to the direction it has been expanded onto an area of the surface at a grazing angle of incidence.
b. rotating the surface about an axis perpendicular to the surface to an angular position wherein light diffracted from the surface and from the pattern on the surface is at a minimum, and
c. detecting the scattered light but not specularly reflected light from at least a portion of said area of said surface with said surface at said angular position wherein the diffracted light is at a minimum.

23. The method claim 22 and further including repeating steps (a) through (c) for another area on the surface.

24. Apparatus for use in detecting particles on a surface of an object comprising:
   a. a holder for holding said object, said holder being mounted for rotational movement,
   b. means for illuminating the surface with a scanning collimated beam of light at grazing angle of incidence, and
   c. camera means positioned above said surface for detecting scattered light from said surface but not specularly reflected light the intensity of the scattered light being proportional to the size of the particles.

25. A method of detecting particles on a surface of an object comprising:
   a. directing a vertically expanded and horizontally scanning collimated beam of light onto the surface of the object at grazing angle of incidence, whereby said particles will scatter light with intensities proportional to the sizes of said particles.
   b. rotating said surface relative to the incident light beam so that diffracted light from said surface itself and any pattern which may be on the surface is reduced to a minimum, and
   c. detecting light scattered from particles which might be present on the surface but not specularly reflected light.

26. The method of claim 24 and wherein detecting scattered light comprises focussing a camera over the area illuminated by the light beam where the intensity is uniform.

* * * * *